United States Patent [19]

Ueno et al.

[11] Patent Number: 5,234,954
[45] Date of Patent: Aug. 10, 1993

[54] TREATMENT OF HYPERLIPIDEMIA WITH 15-KETO-PROSTAGLANDIN COMPOUNDS

[75] Inventors: Ryuji Ueno; Hiroyoshi Osama, both of Hyogo, Japan

[73] Assignee: K.K. Ueno Seiyaku Oyo Kenkyujo, Osaka, Japan

[21] Appl. No.: 899,171

[22] Filed: Jun. 15, 1992

Related U.S. Application Data

[63] Continuation of Ser. No. 557,839, Jul. 26, 1990, abandoned.

[30] Foreign Application Priority Data

Jul. 27, 1989 [JP] Japan .................................. 1-197091
Aug. 7, 1989 [JP] Japan .................................. 1-205352

[51] Int. Cl.$^5$ .................... A61K 31/19; A61K 31/557
[52] U.S. Cl. ............................................ 514/573; 514/824
[58] Field of Search ............................... 514/573, 824

[56] References Cited

U.S. PATENT DOCUMENTS

| | | | |
|---|---|---|---|
| 4,157,341 | 6/1979 | Bindra et al. | 260/559 B |
| 4,278,688 | 7/1981 | Hayashi et al. | 424/305 |
| 4,459,310 | 7/1984 | Dajani | 424/305 |

FOREIGN PATENT DOCUMENTS

| | | |
|---|---|---|
| 0129908 | 1/1985 | European Pat. Off. . |
| 0281239 | 1/1988 | European Pat. Off. . |
| 0284180 | 1/1988 | European Pat. Off. . |
| 0330511 | 2/1988 | European Pat. Off. . |
| 0289349 | 4/1988 | European Pat. Off. . |
| 0293177 | 5/1988 | European Pat. Off. . |
| 0308135 | 9/1988 | European Pat. Off. . |
| 0310305 | 9/1988 | European Pat. Off. . |
| 0342003 | 5/1989 | European Pat. Off. . |
| 0343904 | 5/1989 | European Pat. Off. . |
| 0345951 | 5/1989 | European Pat. Off. . |

OTHER PUBLICATIONS

CA 109:67747m Syntex (U.S.A.), Inc., 1986.
Anggard, Acta physiol. scand, 1966, 66, pp. 509-510.
Robert, et al., Prostaglandins, vol. 11, No. 5, May 1976 pp. 809-828.
Chemical Abstract, vol. 109, 1988–corresponding to JPA 122624.
Chemical Abstract, vol. 110, 1989, 110:891f–corresponding to JPA 286924.
Pharmaceuticals, vol. 110, 1989, p. 431.
Chemical Abstracts, vol. 84, No. 21, 1975, Abstract No. 145224v.

*Primary Examiner*—Frederick E. Waddell
*Assistant Examiner*—Kimberly R. Jordan
*Attorney, Agent, or Firm*—Sughrue, Mion, Zinn, Macpeak & Seas

[57] ABSTRACT

A method for treatment of hyperlipemia which comprises administering, to a subject in need of such treatment, a 15-keto-prostaglandin compound in an amount, effective in decreasing lipid concentration in the blood.

11 Claims, No Drawings

TREATMENT OF HYPERLIPIDEMIA WITH 15-KETO-PROSTAGLANDIN COMPOUNDS

This is a continuation of application Ser. No. 07/557,839 filed Jul. 26, 1990, now abandoned.

BACKGROUND OF THE INVENTION

1. Field of the Invention

The present invention relates to a method for treating hyperlipidemia or inducing decrease in lipid concentration in the blood which comprises administering a 15-ketoprostaglandin compound to a subject.

The object of the present invention is to induce decrease in concentration of triglyceride, cholesterol or phospholipid in the blood of a patient having an elevated concentration of triglyceride, cholesterol or phospholipid in the blood.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

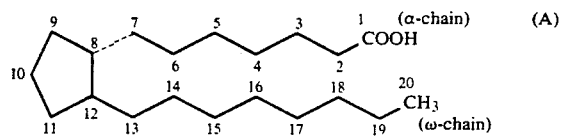

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

| Subscript 1 | 15-OH |
|---|---|
| Subscript 2 | 5,6-unsaturated-15-OH |
| Subscript 3 | 5,6- and 17, 18-diunsaturated-15-OH |

Further, PGFs are sub-classified according to the configration of hydroxy group at 9 into α(hydroxy group being in the alpha configration) and β(hydroxy group being in the beta configration).

2. Background Information $PGE_1$, $PGE_2$ and $PGE_3$ are known to have vasodilating, hypotensive, gastro-juice reducing, intestine-hyperkinetic, uterine contracting, diuretic, bronchodilating and anti-ulcer activities. Also, $PGF_{1\alpha}$, $PGF_{2\alpha}$ and $PGF_{3\alpha}$ are known to have hypertensive, vasocontracting, intestine-hyperkinetic, uterine contacting, luteoregressive and bronchocontracting activities.

In addition, some 15-keto (i.e. having an oxo group at position 15 in place of the hydroxy group) prostaglandins and 13,14-dihydro-15-keto-prostaglandins are known as substances naturally produced by enzymatic actions during metabolism of primary PGs (Acta Physiologica Scandinavica, 66, 509, 1966). It has also been described that 15-keto-prostaglandin $F_{2\alpha}$ has an anti-pregnant activity.

European Patent Application No. 0,310,305 describes that 15-keto-PGEs can be used as catharitics. However, it has not been reported that 15-keto-prostaglandin compounds have an activity inducing decrease in concentration of triglyceride, cholesterol or phospholipid in blood.

As a result of extensive studies about the properties of 15-keto-prostaglandin compounds, the present inventors unexpectedly discovered that these compounds have an activity of inducing decrease in concentration of triglyceride, cholesterol or phospholipid in the blood.

SUMMARY OF THE INVENTION

In a first aspect, the present invention provides a method for treatment of hyperlipidemia which comprises administering, to a subject in need of such treatment, a 15-keto-prostaglandin compound in an amount effective in decreasing lipid concentration in the blood.

In a second aspect, the present invention provides a method for inducing decrease in lipid concentration in the blood which comprises administering, to a subject having an increased lipid concentration in the blood, a 15-keto-prostaglandin compound in an amount effective in inducing decrease in lipid concentration in the blood wherein lipid concentration is increased.

In a third aspect, the present invention provides a use of a 15-ketoprostaglandin compound for the manufacture of a medicament for treatment of hyperlipidemia.

In a fourth aspect, the present invention provides a use of a 15-ketoprostaglandin compound for the manufacture of a medicament for inducing decrease in lipid concentration in the blood of a patient having an increased lipid concentration in the blood.

In a fifth aspect, the present invention provides a pharmaceutical composition for treatment of hyperlipidemia comprising a 15-keto-prostaglandin compound in association with a pharmaceutically acceptable carrier, diluent or excipient.

In a sixth aspect, the present invention provides a pharmaceutical composition for inducing decrease in lipid concentration in the blood of a patient having an increased lipid concentration in the blood comprising a 15-keto-prostaglandin compound in association with a pharmaceutically acceptable carrier, diluent or excipient.

DETAILED DESCRIPTION OF THE INVENTION

"Hyperlipidemia" is a disease which is characterized by the condition wherein lipid concentration in the blood is increased. The lipid in the blood includes triglyceride, (free and total) cholesterol and phospholipid. The above disease is also referred to as hypercholesterolemia, for example, in case wherein the concentration of cholesterol in the blood is increased.

As used herein, the term "treatment" or "treating" refers to any means of control of a disease in a mammal, including preventing the disease, curing the disease, relieving the disease and arresting or relieving the development of the disease.

The term "15-keto-prostaglandin compounds", referred to as 15-keto-PG compounds, include any prostaglandin derivatives which have an oxo group in place of the hydroxy group at position 15 of the prostanoic acid nucleus irrespective of the presence or absence of the double bond between positions 13 and 14.

NOMENCLATURE

Nomenclature of 15-keto-PG compounds herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-keto-PG compounds having 10 carbon atoms in the ω-chain is nominated as 15-keto-20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-keto-PG compounds" includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of 15-keto-PG compounds is based upon the prostanoic acid. These compounds, however, can also be named according to the IUPAC naming system. For example, 13,14-dihydro-15-keto-16R,S-fluoro-PGE₂ is (Z)-7-{(1R,2R,3R)-3-hydroxy-2-[(4R,S)-4-fluoro-3-oxo-1-octyl]-5-oxocyclopentyl}-hept-5enic acid. 13,14-dihydro-15-keto-20-ethyl-11-dehydroxy-11R-methyl-PGE₂ methyl ester is methyl 7-{(1R,2S,3S)-3-methyl-2-[3-oxo-1-decyl]-5-oxo-cyclopentyl}-hept-5-enoate. 13,14-dihydro-6,15-diketo-19-methyl-PGE₂ ethyl ester is ethyl 7-{(1R,2S,3S)-3-hydroxy-2-(7-methyl-3-oxo-1-octyl)-5-oxo-cyclopentyl}-6-oxo-heptanoate. 13,14-dihydro-15-keto-20-ethyl-PGF₂α isopropyl ester is isopropyl (Z)-7-[(1R,2R,3R,5S)-3,5-dihydroxy-2-{3-oxo-1-decyl)-cyclopentyl]-hept-5-enoate. 13,14-dihydro-15-keto-20-methyl-PGF₂α methyl ester is methyl (Z)-7-[(1R,2R,3R,5S)-3,5-dihydroxy-2-{3-oxo-1-nonyl}-cyclopentyl]-hept-5-enonate.

PREFERRED COMPOUNDS

The 15-keto-PGE compounds used in the present invention may be any derivatives of PG insofar as they have an oxo group at position 15 in place of the hydroxy group, and may have a single bond (15-keto-PG1 compounds), a double bond (15-keto-PG2 compounds) between positions 5 and 6, or two double bonds (15-keto-PG3 compounds) between positions 5 and 6 as well as positions 17 and 18.

Typical examples of the compounds used in the present invention are 15-keto-PG, 15-keto-PG, 15-keto-PG, 13,14-dihydro-15-keto-PG, 13,14-dihydro-15-keto-PG, 13,14-dihydro-15-keto-PG, and so on as well as their derivatives.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 6, 16, 17, 19 and/or 20 and compounds having lower alkyl or a hydroxy (lower) alkyl group at position 11 in place of the hydroxy group, of the above PGs.

Examples of substituents present in preferred compounds are as follows: Substituents on the carbon atom at position 3, 17 and/or 19 include lower alkyl, for example, $C_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g. $C_{1-4}$ alkoxy-$C_{1-4}$ alkyl. Substituents on the carbon atom at position 6 include oxo group forming carboxyl. Stereochemistry of PGs having hydroxy, lower alkyl or lower (hydroxy) alkyl substituent on the carbon atom at position 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 16, those having a lower alkyl e.g. methyl, ethyl etc. at position 19, those having an oxo group at position 6, those having a lower alkyl, e.g. methyl, ethyl, etc. at position 20 and those having phenyl or phenoxy which are optionally substituted with halogen or haloalkyl at position 16 in place of the rest of the alkyl chain.

A group of preferred compounds used in the present invention has the formula (I)

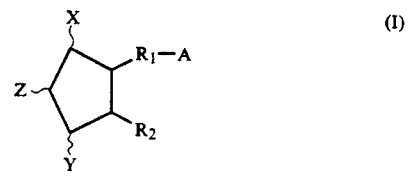

wherein

X and Y are hydrogen, hydroxy, halo, lower alkyl, hydroxy(lower)alkyl, or oxo, with the proviso that at least one of X and Y is a group other than hydrogen, and 5-members ring may have at least one double bond, Z is hydrogen or halogen, A is —CH₂OH, —COCH₂OH, —COOH or its functional derivative, $R_1$ is bivalent saturated or unsaturated, lower or medium aliphatic hydrocarbon residue which is unsubstituted or substituted with halo, oxo or aryl, $R_2$ is saturated or unsaturated, lower or medium aliphatic hydrocarbon residue which is unsubstituted or substituted with oxo, hydroxy, halo, lower alkoxy, lower alkanoyloxy, cyclo(lower)alkyl, aryl or aryloxy, with the proviso the third carbon atom counted from 5-membered ring is substituted with an oxo group.

In the above formula, the term "unsaturated" in the definitions for $R_1$ and $R_2$ is intended to include at least one and optionally more than one double bond and/or triple bond isolatedly, separetely or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 6 to 12 carbon atoms for $R_2$.

The term "halo" denotes fluoro, chloro, bromo and iodo.

The term "lower" is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "hydroxy(lower)alkyl" refers to alkyl as defined above and substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)methane salt, monomethylmonoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyetyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

Preferred examples of A include —COOH, —COOCH$_3$, —COOCH$_2$CH$_3$, —COOCH(CH$_3$)$_2$ and —CONHSO$_2$CH$_3$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-PGs, 13,14-dihydro-15-keto-PGs and their e.g. 6-keto-derivatives, $\Delta^2$-derivatives, 3R,S-methyl-derivatives, 16R,S-methylderivatives, 16,16-dimethyl-derivatives, 16R,S-fluoroderivatives, 16,16-difluoro-derivatives, 17S-methylderivatives, 19-methyl-derivatives, 20-methyl-derivatives and 16-desbutyl-16-phenoxy derivatives.

When 15-keto-PG compounds of the present invention have a saturated bond between positions 13 and 14, these compounds may be in the keto-hermiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparision with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publication (unexamined) No. A-52753/1989.

Alternatively, these compounds may be prepared by a process analogous to that described herein or to known processes.

A practical preparation of the 13,14-dihydro-15-keto compounds involves the following steps; referring to the synthetic charts(I) to (III), reaction of the aldehyde (2) prepared by the Collins oxidation of commercially available (−)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein the ω-chain is a 13,14-dihydro-15-keto-alkyl group is prepared.

Using the above tetrahydropyranyl ether (7), 6-keto-PGE$_1$s (15) of which a group constituted with carbon atoms of position 5, 6 and 7 is

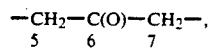

may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at position 9 with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms of position 5, 6 and 7 is

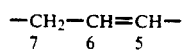

may be prepared in the following steps; as shown in the synthetic chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above tetrahydropyranyl ether (7) as the starting material, the compound having

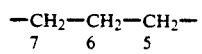

may be prepared by using the same process as that for preparing PGE$_2$ having —CH$_2$CH=CH— and subjecting the resultant compound (18) to catalytic reduction to reduce the double bond between the position 5 and 6 followed by removal of the protective groups.

Synthesis of 5,6-dehydro-PGE$_2$s having

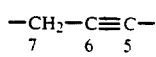

may be carried out by capturing a copper enolate formed by 1,4-addition of a monoalkylcopper complex or a dialkylcopper complex of the following formulae:

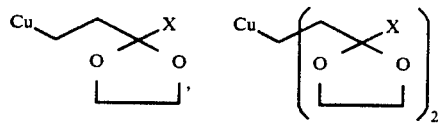

to 4R-t-butyldimethylsilyloxy-2-cyclopenten-1-one with 6-alkoxycarbonyl-1-iodo-2-hexyne or the derivatives.

The 11-β type PGEs can be prepared according to the synthetic chart III.

PGE derivatives having a methyl group at position 11 in place of hydroxy can be prepared by reacting a dimethyl copper complex with PGA-type compound obtained by subjecting 9-hydroxy-11-tosylate to the Jones oxidation. Alternatively, they can be prepared by protecting the carbonyl of saturated ketone (4) produced by reducing unsaturated ketone (3), eliminating p-phenylbenzoyl and tosylating the produced alcohol, treating with DBU to form a lactol, introducing the alpha-chain by Wittig reaction, oxidizing the alcohol at position 9 to give PGA-type compound, and reacting the product with dimethyl copper complex in order to introduce a methyl group into position 11 to give an 11-methyl-PGE-type compound, which on reduction with e.g. sodium borohydride gives an 11-methyl-PGF-type compound. An 11-hydroxymethyl-PGE-type compound, is obtained by a benzophenone-sensitized photoaddition of methanol of PGA-type compound, which is reduced with, e.g. sodium borohydride, to give an 11-hydroxymethyl-PGF-type compound. The synthetic route for the compounds used in the present invention is not limited to the that described above one and may vary using different protecting, reducing and/or oxidizating methods.

Corresponding other PG compounds can be produced analogously.

Synthetic Chart I

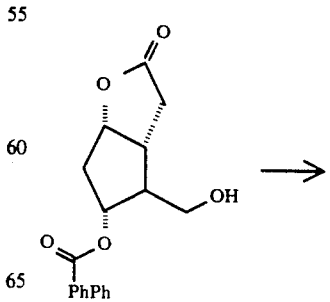

1

9
-continued
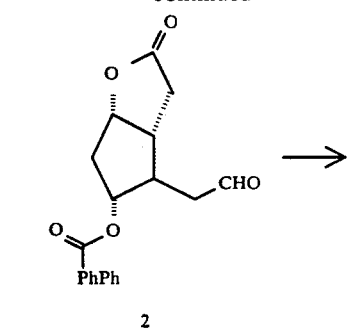
2
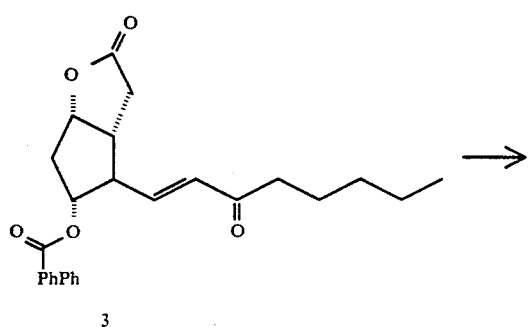
3
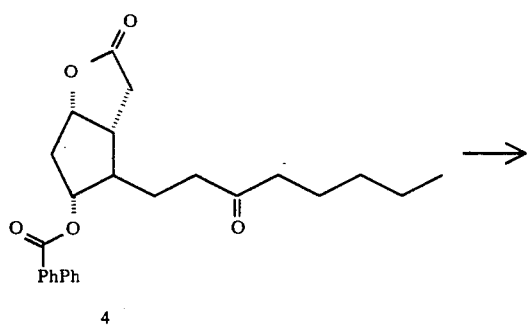
4
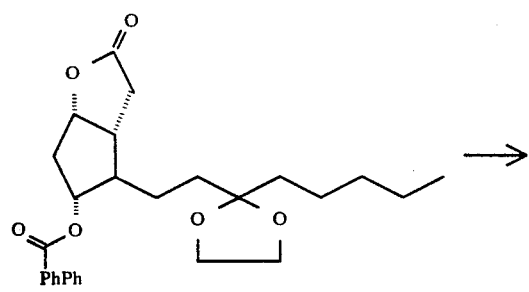
5
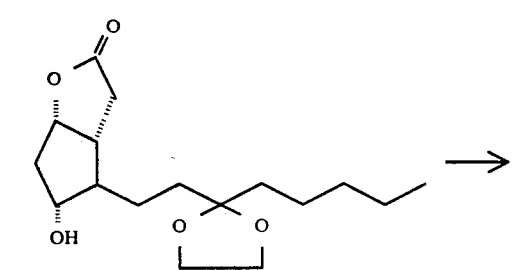
6
10
-continued
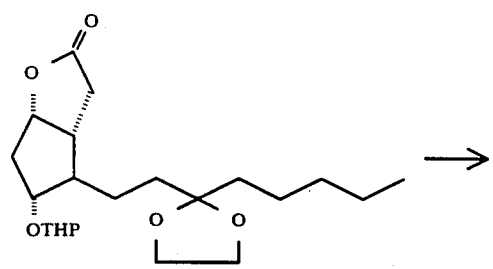
7
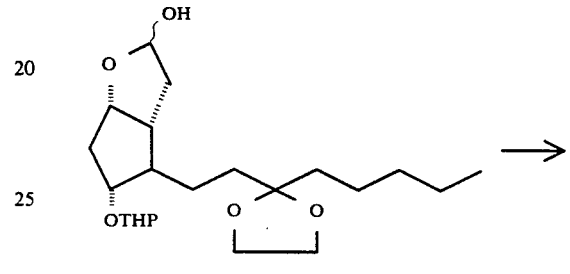
8
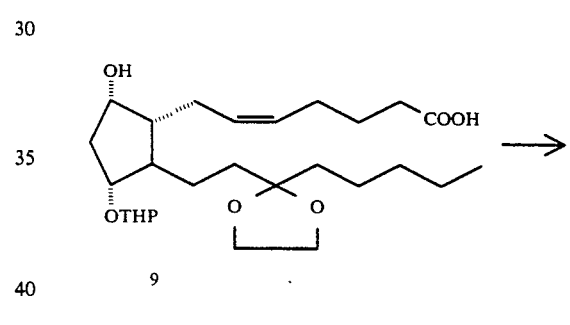
9
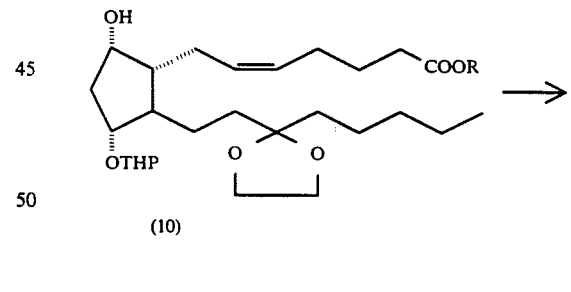
(10)
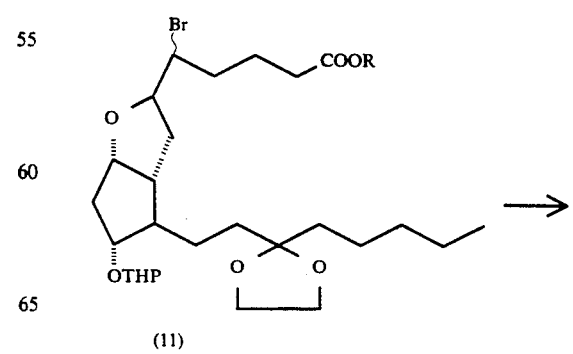
(11)

-continued
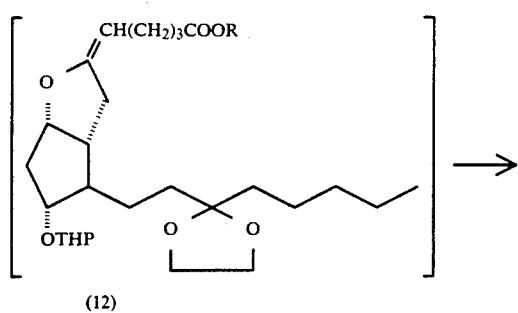
(12)
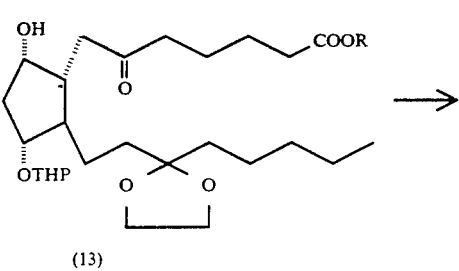
(13)
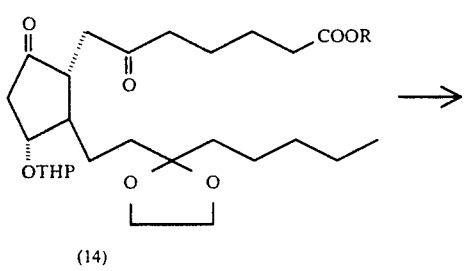
(14)
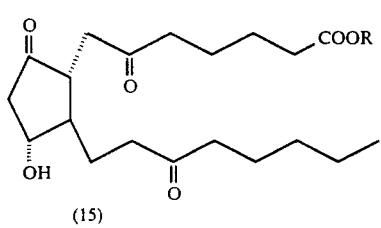
(15)
Synthetic Chart II
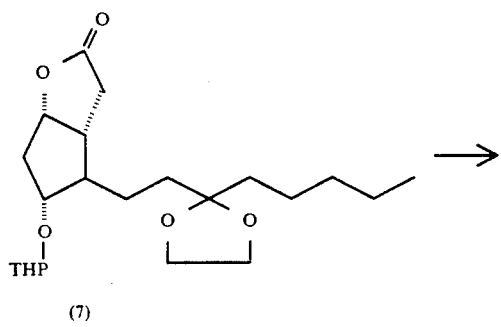
(7)
-continued
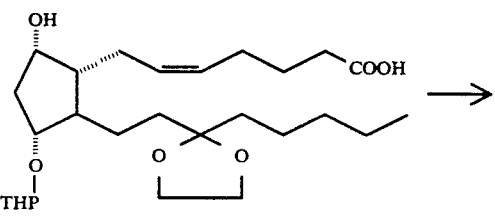
(8)
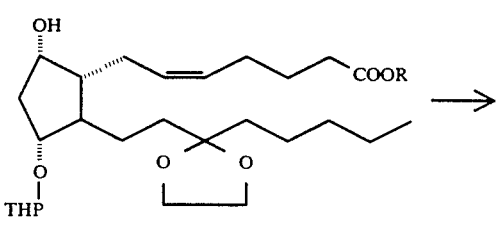
(16)
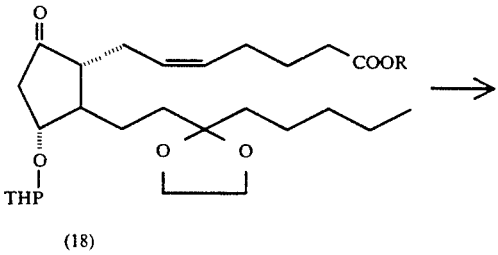
(17)
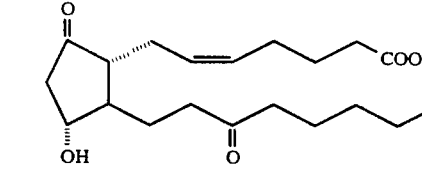
(18)
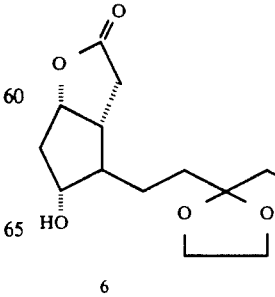
(19)
Synthetic Chart III
6

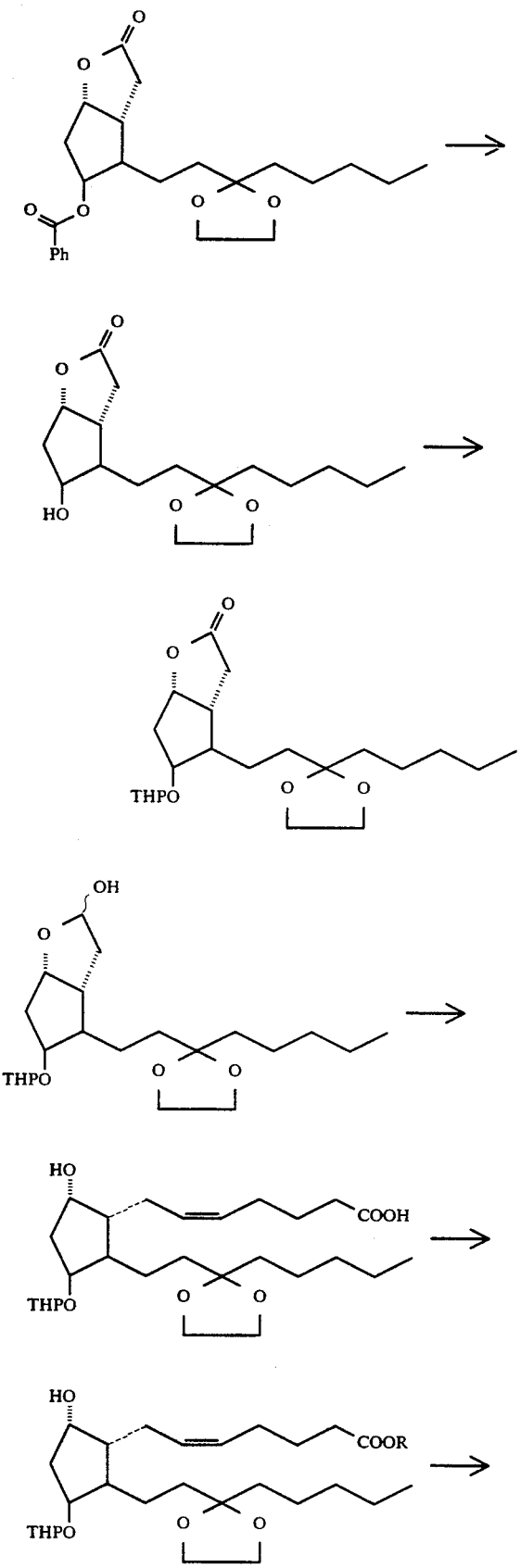

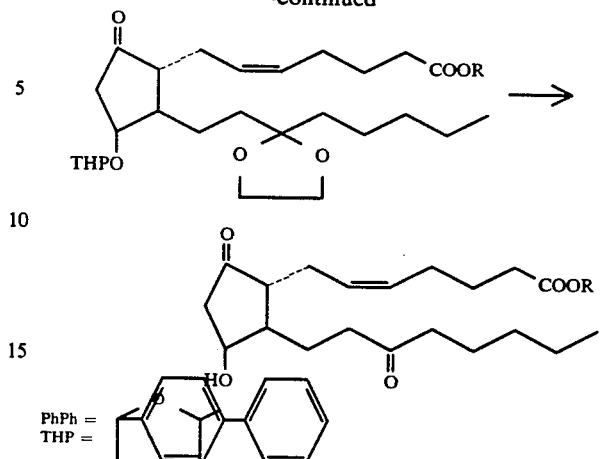

The compounds used in the present invention may be used as a medicine for animals and human beings and usually applied systemically or locally by such methods as oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.001–500 mg/kg administered in 2 to 4 divided doses a day or as a sustained form.

As a solid composition of this invention for oral administration, tablets. troches, buccals, capsules, pills, powders, granules and the like are included. The solid composition containing one or more active substances is mixed with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives other than the inactive diluent, for example, lubricants e.g., magnesium stearae, a disintegrator e.g. cellulose calcium gluconates, stabilizers e.g. α-, β- or γ-cyclodextrins, etherated cyclodextrins (e.g. dimethyl-α-, dimethyl-β-, trimethyl-β-, or hydroxypropyl-β-cyclodextrins), branched cyclodextins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediated effect is desired. For this purpose, base e.g. glycerine, lactose may be used.

Liquid compositions for oral administration include pharmaceutically acceptable emulsions, solutions, suspensions, syrups, elixirs and the like and contain a generally used inactive diluent e.g. purified water or ethyl alcohol. The composition may contain additives e.g. wetting agents, suspending agents, sweeteners, flavors, perfumes and preservatives.

The composition of the present invention may be sprays which may contain one or more active ingredients and which can be prepared according to a well known methods.

An injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria- retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

The compounds used in the medicament for treatment of hyperlipidemia or for inducing decrease in lipid concentration according to the present invention have an effect of decreasing blood level of triglyceride, cholesterol or phospholipid. One mechanism of the action of said compounds is related to excretion of triglyceride, cholesterol or phospholipid in the blood. This, in turn, is based on the action of the compounds promoting release into intestine or release with feces of triglyceride, cholesterol or phospholipid in the blood. Accordingly, the compounds used in the present invention are useful for treatment, e.g. prevention, therapeutic treatment, prevention or delay of worsening of abnormal cholesterol level, abnormal triglyceride level or abnormal phospholipid level in the serum, irrespective of cause, e.g. disease, drug or food. Further, the compounds used in the present invention are adapted for the treatment of said abnormalities accompanied by obesity.

A more complete understanding of the present invention can be obtained by reference to the following Formulation Examples and Test Examples which are provided herein for purpose of illustration only and are not intended to limit the scope of the invention.

FORMULATION EXAMPLE 1

| (Hard gelatin capsules) | |
| --- | --- |
| 13,14-dihydro-15-keto-16R,S-fluoro-PGE$_2$ | 50 mg |
| lactose | 200 mg |

The above ingredients were mixed and filled in hard gelatin capsules.

FORMULATION EXAMPLE 2

| (Powders for injection) | (Parts by weight) |
| --- | --- |
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

FORMULATION EXAMPLE 3

| (Injectable solution) | (Parts by weight) |
| --- | --- |
| 13,14-dihydro-15-keto-16,16-dimethyl-PGE$_2$ | 0.2 |
| nonion surfactant | 2 |
| distilled water | 98 |

The above ingredients were mixed and sterilized to give and injectable solution.

FORMULATION EXAMPLE 4

13,14-dihydro-15-keto-16,16-difluoro-20-ethyl-PGE$_2$ (50 mg) dissolved in methanol (10 ml) was mixed with mannitol (18.5 g). The mixture was screened (with a sieve, the pore size of which being 30 mm in diameter), dried and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16,16-difluoro-20-ethyl-PGE$_2$ per capsule.
* Trade Mark

FORMULATION EXAMPLE 5

| (Powders for oral administration) | (Parts by weight) |
| --- | --- |
| 13,14-dihydro-15-keto-16,16-difluoro-PGF$_{2\alpha}$ methyl ester | 5 |
| light anhydrous silicic acid | 5 |
| Abicel* | 20 |
| lactose | 70 |

*Trade Mark

The above ingredients were mixed to give powders for oral administration.

FORMULATION EXAMPLE 6

| (Soft gelatine capsules) | (Parts by weight) |
| --- | --- |
| 13,14-dihydro-15-keto-20-methyl-PGE$_2$ methyl ester | 1 |
| light anhydrous silicic acid | 899 |
| Panasate | 20 |

*Trade Mark

The above ingredients were mixed and filled in soft gelatine capsules.

FORMULATION EXAMPLE 7

(Enteric capsules)

16-desbutyl-13,14-dihydro-15-keto-16-(m-trifluorocmethyl)phenoxy-PGF$_{2\alpha}$ methyl ester (50mg) dissolved in methanol (10 ml) was mixed with mannitol (18.5 g). The mixture was screened (with a sieve, the pore size of which being 30 mm in diameter), dried for 90 minutes at 30° C. and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16-desbutyl-16-m-trifluoromethylphenoxy-PGF$_{2\alpha}$ methyl ester per capsule.
* Trade Mark In the above formulation examples, the active ingredient can be replaced by any other compound within the compounds used in the invention.

TEST EXAMPLE 1

The results are shown in the following Tables, in which * denotes P<0.1,  P<0.05 and * P<0.01.

TABLE 1

| | Body Weight and Water Intake | | | | | | | |
|---|---|---|---|---|---|---|---|---|
| | Body weight | | | | Water Intake | | | |
| | Control | | Medicated | | Control | | Medicated | |
| Day | Mean | S.D. | Mean | S.D. | Mean | S.D. | Mean | S.D. |
| −2 | 316 | ±20 | 322 | ±12 | | | | |
| −1 | 317 | ±26 | 330 | ±15 | 84.7 | ±20.4 | 101.9 | ±14.0 |
| 0 | 307 | ±42 | 324 | ±10 | | | | |
| 1 | 316 | ±35 | 325 | ±14 | 98.6 | ±19.1 | 53.3 | ±12.2 |
| 2 | 315 | ±31 | 321 | ±21 | 98.6 | ±19.1 | 53.3 | ±12.2 |
| 3 | 317 | ±27 | 320 | ±31 | 87.8 | ±12.1 | 62.7 | |
| 4 | 320 | ±24 | 328 | ±31 | 100.0 | | 76.2 | ±26.8 |
| 5 | 322 | ±27 | 327 | ±35 | 96.0 | ±14.8 | 68.6 | ±19.7 |
| 6 | 327 | ±28 | 333 | ±33 | 96.0 | ±14.8 | 68.6 | ±17.7 |
| 7 | 331 | ±25 | 347 | ±36 | 94.7 | ±18.8 | 78.3 | ±13.9 |
| 8 | 321 | ±21 | 334 | ±30 | 94.7 | ±18.8 | 78.3 | ±13.9 |
| 9 | 315 | ±30 | 342 | ±25 | | | | |
| 10 | 316 | ±35 | 341 | ±26 | 82.3 | ±10.0 | 105.8 | ±2.8 |
| 11 | 317 | ±38 | 335 | ±30 | 82.3 | ±10.7 | 105.8 | ±2.8 |
| 12 | 324 | ±27 | 347 | ±31 | 96.8 | ±13.4 | 94.4 | ±17.7 |
| 13 | 320 | ±25 | 356 | ±31 | | | | |
| 14 | 333 | ±31 | 349 | ±34 | 96.8 | ±13.4 | 94.4 | ±17.7 |

TABLE 2

| | | Assay of Serum | | | | | | |
|---|---|---|---|---|---|---|---|---|
| | | TP g/d | ALB g/d | GLU g/d | PL g/d | F-CHO g/d | T-CHO g/d | TG g/d |
| Control | Mean | 5.2 | 3.4 | 171 | 227 | 35 | 152 | 177 |
| | S.D. | ±0.5 | ±0.4 | ±26 | ±11 | ±2 | ±12 | ±44 |
| Medicated (3.0 mg/kg) | Mean | 5.8 | 3.7 | 184 | 161** | 25** | 113** | 65*** |
| | S.D. | ±0.3 | ±0.2 | ±33 | ±31 | ±4 | ±23 | ±18 |

Male Wistar rats (8 weeks old) were anesthetized by pentobarbital (40 mg/kg, i.p.) and cortex of the left kidney was partly excised. After 3 to 7 days, the right kidney was totally excised. The over all excision of the kidney was 1 plus three fourth to 1 plus four fifth. As the test compound, 13,14-dihydro-15-keto-16R,S-fluoro-PGE$_2$ was suspended in distilled water, homogenized by sonication and orally administered, at a rate of 3 mg/kg/ml, continuously for a period of two weeks starting from the day after two weeks of the excision of the kidneys (three animal per group). The control group orally received the same volume of distilled water.

Feces were collected imediately, two days and two weeks after the administration and the intestinal contents were collected two weeks after the administration. These were assayed for excretion of triglyceride (TG), phospholipid (PL), free cholesterol (F-CHO) and total cholesterol (T-CHO).

In addition, blood samples were collected from a jugular vein without anesthesia one week after the administration and assayed for total protein (TP), albumin(ALB), glucose (GLU), triglyceride, phospholipid, free cholesterol and total cholesterol. Also, body weight and water intake were measured from a day before the experiment to the last day of the experiment.

From the above results, it can be easily understood that phospholipid, free cholesterol, total cholesterol and triglyceride in the blood was significantly decreased in the medicated group.

Almost no influence was observed in the medicated group in respect to body weight and water intake.

Further, no differences were noted between the control and medicated groups in respect to total protein, albumin and glucose in the blood as well as general nutritive conditions.

TABLE 3

| | | | Assay of Feces | | |
|---|---|---|---|---|---|
| Day | | | PL mg | F-CHO mg | T-CHO mg |
| 2 | Control | Mean | 0.06 | 0.08 | 0.01 |
| | | S.D. | ±0.02 | ±0.012 | ±0.04 |
| | Medicated | Mean | 0.42 | 0.32** | 0.37** |
| | | S.D. | ±0.02 | ±0.012 | ±0.04 |
| | Control | Mean | 0.03 | 0.02 | 0.03 |
| | | S.D. | ±0.02 | ±0.02 | ±0.02 |
| | Medicated | Mean | 0.35** | 0.33*** | 0.37*** |
| | | S.D. | ±0.04 | ±0.06 | ±0.08 |

TABLE 4

| | | Triglyceride in Feces and Intestinal contents | | | | | |
|---|---|---|---|---|---|---|---|
| | | Day | | | | | |
| | | 2 | | 7 | | 14 | |
| | | Control | Medi. | Control | Medi. | Control | Medi. |
| TG (mg) | Mean | 0.07 | 0.33 | 0.08 | 0.63*** | 35.07 | 146.30*** |
| | S.D. | ±0.02 | ±27 | ±0.05 | ±0.07 | ±3.06 | ±18.93 |

TEST EXAMPLES 2

The procedure of Test Example 1 was repeated except that 13,14-dihydro-15-keto-16,16-difluoro-$PGE_2$ (1.0 mg/kg) was used as the test compound. Assays were performed with the feces at day 5, the intestinal contents at day 14 and the serum at day 14. The results are shown in the following Tables.

TABLE 5

| Day | | | Assay of Feces | | |
|---|---|---|---|---|---|
| | | | T-CHO mg | TG mg | PL mg |
| 5 | Control | Mean | 0.13 | 0.35 | 0.10 |
| | | S.D. | ±0.05 | ±0.36 | ±0.04 |
| | Medicated | Mean | 0.60** | 1.08 | 0.60* |
| | | S.D. | ±0.36 | ±1.03 | ±0.49 |

TABLE 6

| Day | | | Assay of Intestinal Contents | | |
|---|---|---|---|---|---|
| | | | T-CHO mg | TG mg | PL mg |
| 14 | Control | Mean | 0.36 | 6.71 | 2.05 |
| | | S.D. | ±0.08 | ±4.91 | ±1.14 |
| | Medicated | Mean | 0.62** | 18.95** | 10.91*** |
| | | S.D. | ±0.25 | ±9.86 | ±1.66 |

TABLE 7

| Day | | | Assay of Serum | | |
|---|---|---|---|---|---|
| | | | T-CHO mg/dl | TG mg/dl | PL mg/dl |
| 14 | Control | Mean | 116 | 101 | 168 |
| | | S.D. | ±4 | ±32 | ±3 |
| | Medicated | Mean | 93* | 90 | 135* |
| | | S.D. | ±22 | ±49 | ±32 |

TEST EXAMPLE 3

Crj: Wistar rats were used at 5 animals per group. As the test compound, 13,14-dihydro-15-keto-20-ethyl-$PGF_{2\alpha}$ isopropyl ester was dissolved in the physiological saline and subcutaneously administered once a day at dorsal skin at a volume of 5 ml/kg for continuous 14 days. The dose of the test compound was 20 mg/kg/day. The control group received the same amount of the physiological saline. After 14 days, the concentration of triglyceride (TG) in the serum was measured. The results are shown in the following Table.

TABLE 8

| | | Assay of Serum |
|---|---|---|
| | | TG mg/dl |
| Control | Mean | 114 |
| | S.D. | ±23.8 |
| Medicated | Mean | 80 |
| | S.D. | ±14.3 |

From the above results, it can be clearly seen that triglyceride, cholesterol and phospholipid are significantly excreted in the feces or the intestinal contents of the medicated animals.

What we claim is:

1. A method for treatment of hyperlipidemia which comprises administering, to a subject in need of such treatment, a 15-keto-16-mono- or di-haloprostaglandin compound in an amount effective in decreasing liquid concentration in the blood, said 15-keto prostaglandin compound being selected from compounds of the following formula (I):

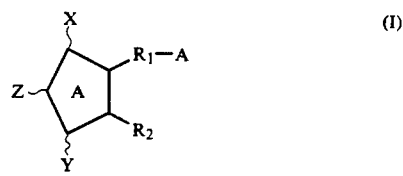

wherein X and Y are independently selected from the group consisting of hydrogen, hydroxy, halo, lower alkyl, hydroxy(lower)alkyl and oxo, with the proviso that at least one of X and Y is not hydrogen and said ring A may contain at least one double bond; Z is hydrogen or halogen; A is —$CH_2OH$, —$COCH_2OH$, —COOH or a functional derivative thereof; $R_1$ is a bivalent saturated or unsaturated, lower or medium aliphatic hydrocarbon residue which is unsubstituted or substituted with halo, oxo or aryl, $R_2$ is a saturated or unsaturated, lower or medium aliphatic hydrocarbon residue which is unsubstituted or substituted with oxo, hydroxy, halo, lower alkoxy, lower alkanoyloxy, cyclo(lower)alkyl, aryl or aryloxy, with the proviso that $R_2$ contains at least four carbon atoms, with the third carbon atom of $R_2$ removed from ring A being substituted with an oxo group and the fourth carbon atom of $R_2$ removed from ring A being substituted with one or two halogen atoms.

2. The method according to claim 1, in which lipid decrease is triglyceride, cholesterol or phospholipid.

3. The method according to claim 1, for treatment of hypercholesterolemia.

4. The method according to claim 1, in which said 15-keto-16-mono- or di-haloprostaglandin compound is a 13,14-dihydro-16-mono- or di-halo-15-ketoprostaglandin compound.

5. The method according to claim 1, in which said 15-keto-16-mono- or di-haloprostaglandin compound is a 5,15-diketoprostaglandin compound.

6. A method for inducing decrease in lipid concentration in the blood which comprises administering, to a subject having an increased lipid concentration in the blood, a 15-keto-16-mono- or di-haloprostaglandin compound in an amount effective in inducing decrease in lipid concentration in the blood wherein lipid concentration is increased, said 15-keto prostaglandin compound being selected from compounds of the following formula (I):

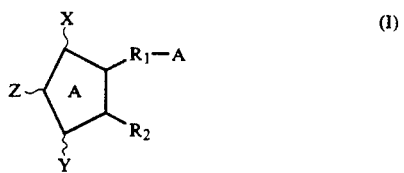

wherein X and Y are independently selected from the group consisting of hydrogen, hydroxy, halo, lower alkyl, hydroxy(lower)alkyl and oxo, with the proviso that at least one of X and Y is not hydrogen and said ring A may contain at least one double bond; Z is hydrogen or halogen; A is —$CH_2OH$, —$COCH_2OH$, —COOH or a functional derivative thereof; $R_1$ is a bivalent saturated or unsaturated, lower or medium aliphatic hydrocarbon residue which is unsubstituted or substituted with halo, oxo or aryl, $R_2$ is a saturated or unsaturated, lower or medium aliphatic hydrocarbon residue which is unsubstituted or substituted with oxo, hydroxy, halo, lower alkoxy, lower alkanoyloxy, cyclo(lower)alkyl, aryl or aryloxy, with the proviso that $R_2$ contains at least four carbon atoms, with the third carbon atom of $R_2$ removed from ring A being substituted with an oxo group and the fourth carbon atom of $R_2$ removed from ring A being substituted with one or two halogen atoms.

7. The method according to claim 6, in which lipid decrease is triglyceride, cholesterol or phospholipid.

8. The method according to claim 6, for treatment of hyperlipemia.

9. The method according to claim 6, for treatment of hypercholesterolemia.

10. The method according to claim 6, in which said 15-keto-16-mono- or di-haloprostaglandin compound is a 13,14-dihydro-16mono- or di-halo-15-ketoprostaglandin compound.

11. The method according to claim 6, in which said 15-keto-16-mono- or di-haloprostaglandin compound is a 6,15-diketo-prostaglandin compound.

* * * * *